(12) United States Patent
Shimaoka

(10) Patent No.: US 6,417,920 B1
(45) Date of Patent: Jul. 9, 2002

(54) PARTICLE SIZE ANALYZER BASED ON LASER DIFFRACTION METHOD

(75) Inventor: Haruo Shimaoka, Nara (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/699,338

(22) Filed: Oct. 31, 2000

(30) Foreign Application Priority Data

May 11, 1999 (JP) ............................................ 11-316030
May 11, 1999 (JP) ............................................ 11-316031

(51) Int. Cl.[7] .......................... G01D 15/02; G01D 21/00
(52) U.S. Cl. ....................................... 356/336; 356/338
(58) Field of Search ................................. 356/335, 336, 356/337, 338, 340, 342, 343; 250/574, 573, 222.2

(56) References Cited

U.S. PATENT DOCUMENTS

| 3,713,743 A | * | 1/1973 | Simms | 356/208 |
| 5,007,737 A | * | 4/1991 | Hirleman, Jr. | 356/336 |
| 5,105,093 A | * | 4/1992 | Niwa | 250/574 |
| 5,164,787 A | * | 11/1992 | Igushi et al. | 356/336 |
| 5,185,641 A | * | 2/1993 | Igushi et al. | 356/336 |
| 5,379,113 A | * | 1/1995 | Niwa | 356/336 |
| 5,400,139 A | * | 3/1995 | Shimaoka | 356/336 |
| 5,461,476 A | * | 10/1995 | Fournier | 356/343 |
| 5,540,494 A | * | 7/1996 | Purvis, Jr. et al. | 356/73 |
| 5,796,480 A | * | 8/1998 | Igushi | 356/336 |
| 5,999,250 A | * | 12/1999 | Hairston et al. | 356/73 |

* cited by examiner

Primary Examiner—Michael P. Stafira
(74) Attorney, Agent, or Firm—Kanesaka & Takeuchi

(57) ABSTRACT

A particle size analyzer based on laser diffraction method is formed of an irradiation optical system for irradiating laser beam to particles, a measurement optical system for measuring a space intensity distribution by receiving light diffracted/scattered by the particles of the laser beam from the irradiation optical system, and an operation portion for obtaining a particle size distribution of the particles from the results measured by the measurement optical system. The irradiation optical system has a semiconductor laser in an output beam wavelength of 300 to 500 nm as a light source. Thus, particles having diameters of the order of sub-microns can be measured.

2 Claims, 10 Drawing Sheets

PARTICLE SIZE ANALYZER BASED ON LASER DIFFRACTION METHOD

BACKGROUND OF THE INVENTION AND RELATED ART STATEMENT

The invention relates to a particle size analyzer based on a laser diffraction method, more particularly, a particle size analyzer capable of accurately measuring a wide range of particles having a fine diameter of the order of 0.1 μm to a large diameter of the order of several thousands μm.

In a particle size analyzer based on the laser diffraction method, generally, a particle size distribution of particles to be measured can be calculated through measuring a space intensity distribution of diffracted/scattered light obtained by irradiating laser light to the particles to be measured in a dispersing/flying As state; and calculating the measured results based on a Mie's scattering theory and a Fraunhofer's diffraction theory.

More specifically, in a basic structure of a measuring portion of the measuring apparatus of this type as diagrammatically shown in FIG. 6, when laser beam from a laser light source 41 is irradiated to a particle group P to be measured through a collimating lens 42 to be parallel beam, the laser beam is diffracted or scattered by the particle group P to be measured to thereby form a spacial light intensity distribution pattern. Among the diffracted/scattered light (hereinafter simply referred to as "scattered light"), the forward scattered light is converged by a lens 53a to form ring-shape scattered images on a detection plane disposed at a focal distance position. The forward scattered light intensity distribution pattern is detected by a ring detector (forward scattered light sensor) 53b formed of a plurality of light sensor elements having ring-shape light receiving surfaces of different radii arranged concentrically. Also, the sideward and backward scattered light is detected by sideward scattered light sensors 54 and backward scattered light sensors 55.

The space intensity distribution pattern of the scattered light measured at the measuring portion by the plural light sensors is digitized by the A/D converter and inputted to a computer as the scattered light intensity distribution data.

The scattered light intensity distribution data are varied depending on the size of the particles. Since different size particles are mixed in the actual particle group P to be measured, the intensity distribution data of the scattered light by the particle group P are formed by laying one scattered light on top of the other, respectively. When this situation is expressed by a matrix, Equation (1) can be obtained:

$$s = Aq \quad (1)$$

wherein, $$s = \begin{pmatrix} s_1 \\ s_2 \\ \vdots \\ s_m \end{pmatrix}, \quad q = \begin{pmatrix} q_1 \\ q_2 \\ \vdots \\ q_n \end{pmatrix} \quad (2)$$

$$A = \begin{pmatrix} a_{1,1} & a_{1,2} & \cdots & \cdots & \cdots & a_{1,n} \\ a_{2,1} & & & & & \\ \vdots & & & a_{i,j} & & \\ a_{m,1} & \cdots & \cdots & \cdots & \cdots & a_{m,n} \end{pmatrix} \quad (3)$$

s (vector) is intensity distribution data (vector) of the scattered light. Their elements $s_i$ (i=1, 2, ... m) are incident light quantities detected by the respective elements of the ring detector 53b, and sideward and backward scattered light sensors 54, 55.

q (vector) is particle size distribution data (vector) expressed as a frequency distribution %. A region of diameters of the particle group to be measured (maximum particle diameter: $X_1$, minimum particle diameter: $X_{n+1}$ are divided into n, and the respective particle diameter intervals are represented by ($X_j$, $X_{j+1}$) (j=1, 2, ... n). The elements $q_j$ (j=1, 2,... n) of the q (vector) are the particle quantities corresponding to the particle diameter intervals ($X_j$, $X_{j+1}$). Normally, it is normalized to be the following Equation (4).

$$\sum_{j=1}^{n} q_j = 100\% \quad (4)$$

A (matrix) is a coefficient matrix for converting the particle size distribution data (vector) q to light intensity distribution data (vector) s. The physical meaning of elements $a_{i,j}$ (i=1, 2, ... m, j=1, 2, ... n) of A (matrix) is an incident light quantity with respect to the i-th element of light scattered by the particles of a unit particle quantity belonging to the particle diameter interval ($X_j$, $X_{j+1}$).

A numeral value of $a_{i,j}$ can be theoretically calculated beforehand. In case the diameter of the particle is sufficiently large when compared with a wavelength of the laser beam as the light source, Fraunhofer's diffraction theory is used. However, in a region where the diameter of the particle is shorter than or the same as the wavelength of the laser beam, i.e. sub-micron region, it is necessary to use Mie's scattering theory. The Fraunhofer's diffraction theory can be considered to be an excellent approximate of the Mie's scatting theory effective in case the particle diameter is sufficiently large when compared with the wavelength in a forward fine-angle scattering.

In order to calculate the elements of a constant matrix A by using the Mie's scatting theory, it is necessary to set the absolute refractive indexes, i.e. complex numbers, of particles and a medium, i.e. medium liquid, in which the particles are dispersed. There may be a case where a relative refractive index, i.e. complex number, of the particles and the medium is set, instead of setting the respective refractive indexes.

As an equation for obtaining the least square integral of the particle size distribution data (vector) q based on the above equation (1), the following equation is obtained:

$$q = (A^T A)^{31\ 1} A^T S \quad (5)$$

wherein, $A^T$ is a transpose of A, and $(\ )^{-1}$ is an inverse matrix.

The respective elements of the light intensity distribution data (vector) s in the right side of Equation (5) are numeral values detected by the ring detector 53b, sideward scattered light sensors 54 and backward scattered light sensors 55. Also, the coefficient matrix A can be obtained beforehand by using the Fraunhofer's diffraction theory or the Mie's scattering theory. Therefore, when the calculation of Equation (5) is carried out by using the known data, it is apparent that the particle size distribution data (vector) q can be obtained.

The above explanation is a basic measuring theory of the particle size distribution measurement based on the laser diffraction method. Incidentally, the above-explained method is one example of methods for calculating the particle size distribution, and there are many other variations in measuring methods and kinds and arrangements of the sensors and detectors.

Here, in the conventional particle size analyzer based on the laser diffraction method, a laser beam source having a wavelength of 600 to 800 nm is used as a laser beam source 41, as shown in FIG. 6. With the laser beam having such a wavelength, a particle size distribution in a particle diameter region of the order of sub-sub-micron less than 0.1 $\mu$m can not be measured.

A specific structure of a conventional particle size analyzer based on the laser diffraction method is shown as a block diagram in FIG. 7. The particle size analyzer in this example comprises an irradiation optical system 51 including a semiconductor laser 51a and a collimating lens 51b allow output beam therefrom to become parallel beam; and a measurement optical system 56 including a flow cell 52 wherein a suspension in which a sample P to be measured is dispersed in a medium liquid flows, a forward scattered light sensor formed of a converging lens 53a for detecting only the light diffracted/scattered in a predetermined front angle region among the diffracted/scattered light by the particle group P to be measured and a ring detector 53b, sideward scattered light sensors 54 and backward scattered light sensors 55 for detecting the light diffracted/scattered sideward and backward among the light diffracted/scattered by the particle group P to be measured, respectively. Then, outputs from the respective light sensors are amplified and digitized at a data sampling circuit 57 including amplifiers and A/D converters corresponding thereto, and then inputted to a computer 58. In the computer 58, a particle size distribution of the particle group P to be measured can be obtained through the above-stated operation by using a space intensity distribution data of the diffracted/scattered light formed of the entire outputs of the respective light sensors, and the results are outputted to a display device 59 or a printer 60 to display or print out thereof.

Here, as a light source of the irradiation optical system 51, a laser other than the semiconductor laser 51a as in the above example may be used. However, in either case, a wavelength of the output beam is in a range from 600 to 800 nm.

Incidentally, in the conventional particle size analyzer as shown in FIG. 7, the reason why the sideward and backward scattered light sensors 54 and 55 are provided in addition to the forward scattered light sensor 53 as the measurement optical system 56 is to make the measuring lower limit of the particle size distribution smaller, so that the measuring region is extended to a particle size of the order of sub-micron. In other words, there is a tendency such that in the space intensity distribution of the light scattered by the particle group to be measured, as the particle diameter becomes smaller, the beam intensity of a large scattering angle becomes stronger. Thus, in case particles with small diameters are measured, it is necessary to measure the space intensity distribution of the scattered light in a wide angle range by also detecting the sideward and backward scattered light. In case a laser beam having a wavelength of the order of 600 to 800 nm is used as a light source of the irradiation optical system as in the conventional apparatus, without the backward and sideward scattered light sensors, particles having diameters of the order of sub-micron can not be measured.

Thus, in the conventional particle size analyzer wherein particles having diameters of the order of sub-micron can be measured, as shown in FIG. 7, in addition to the forward scattered light sensor, it is essential to provide the sideward and backward scattered light sensors, so that the structure of the measurement optical system becomes complicated and the cost of the apparatus is raised.

Also, as the forward scattered light sensor, in case the converging lens and the ring detector are used, only if an optical axis coincides with respect to the irradiation optical system, an accurate measurement can be made. However, in the sideward and backward scattered light sensors, since it is necessary that each light sensor is accurately set in an angle with respect to the light irradiation position against the particle group to be measured, it is required to hold a fixed relative positional relationship of the sample cell containing or flowing therethrough the particle group to be measured with the irradiation optical system and the measurement optical system. For example, in case particles with the diameters in the order of sub-micron floating in air or water are measured, there has been a problem wherein a measurement in an open system without using the sample cell can not substantially be carried out.

Also, as shown in FIG. 8, a particle size analyzer has been practically used, which includes two systems, i.e. an irradiation optical system and a measurement optical system, enabling to measure particles having diameters less than 0.1 $\mu$m.

More specifically, as the irradiation optical system, in addition to a semiconductor laser 51a having a wavelength region as described above, there are provided a light source 61 capable of outputting beam having a wavelength shorter than the laser and a filter 61a, so that the light sources 51a and 61 selectively irradiate a sample cell 52 wherein a suspension in which a particle group P to be measured is dispersed in a medium flows or is contained. At the same time, in addition to a forward scattered light sensor 53b, sideward scattered light sensors 54 and backward scattered light sensors 55 which are the measurement optical system for the semiconductor laser light source 51a, there are provided sideward scattered light sensors 62 and backward scattered light sensors 63 which are the measurement optical system for the light source 61, and outputs from the respective light sensors are inputted to a computer 58 through a data sampling circuit 57 including amplifiers and A/D converters corresponding to the respective sensors. In the computer 58, a particle size distribution in a region of particle diameters of the order of sub-micron is calculated from space intensity distribution data of the scattered light obtained from the semiconductor laser 51a and the measurement optical system corresponding thereto, and at the same time a particle size distribution having smaller particle diameters in the order of sub-sub-micron is calculated from the space intensity distribution data of the scattered light obtained from the light source 61 and the measurement optical system corresponding thereto.

Also, as an apparatus based on another method for measuring particle diameters in a region less than 0.1 $\mu$m, an apparatus has been practically used, wherein a particle size analyzer based on the light diffraction method using a laser beam source having a red color wavelength region is used in combination with a photon correlation method, i.e. dynamic light scattering method, taking advantage of a periodic information of a Brownian movement.

All the conventional particle size analyzer enabling to measure particle diameters in a region of the order of sub-sub-micron can not accurately measure a particle size distribution in a particle group to be measured. More specifically, in the apparatus including the above-described two systems, such as the irradiation optical system and the measurement optical system, or the particle size analyzer wherein the measuring method based on a theory different from the laser diffraction method is jointly used, the measured results of the particle size distribution have breakpoints without fail, so that accurate particle size distribution of the particle group to be measured can not be obtained. Here, since the particle size distribution generally relies on its measuring method, even if measured results obtained based on different measuring methods are combined together, the result is meaningless.

Also, in case particles of a pigment, dye or ink are measured, the blue color particles easily absorb the red color laser beam and, especially, particles in a region of sub-micron have such a conspicuous tendency. Therefore, there has been a problem such that an accurate particle size distribution of a blue color particle group can not be measured by the conventional particle size analyzer using irradiation of the red color laser beam.

An object of the present invention is to provide a particle size distribution measuring apparatus, wherein even if a structure of a measurement optical system is simplified, particles having diameters of the order of sub-micron can be measured as in the conventional measuring apparatus, so that although the particle to size analyzer of the invention has the same performance as that of the conventional measuring apparatus, the apparatus cost can be reduced.

Another object of the invention is to provide a particle size analyzer, wherein even if the measurement optical system and the irradiation optical system are separated, particles having diameters in the order of sub-microns can be measured, so that the particles having diameters of the order of sub-micron can be measured in an open system without using a cell.

A further object of the invention is to provide a particle size analyzer based on the laser diffraction method, wherein a particle size distribution of a particle group to be measured including even blue color particles can be accurately measured continuously in a wide range of the order from a sub-sub-micron to several thousands of $\mu$m.

SUMMARY OF THE INVENTION

In order to attain the above objects, a particle size analyzer based on the laser diffraction method of the invention includes an irradiation optical system for irradiating laser beam to a particle group in a dispersing state; a measurement optical system for receiving light, diffracted/scattered by the particles, of the laser beam irradiated from the irradiation optical system, and measuring a space intensity distribution; and an operating portion for calculating a particle size distribution of the particle group from the measurement results obtained at the measurement optical system, wherein a light source in the irradiation optical system is a semiconductor laser having an output beam wavelength in a range of from 300 to 500 nm.

In the invention, only a laser diffraction method is used; laser beam of a single wavelength in a range of 300 to 500 nm is used as light to be irradiated to the particle group to be measured; and the space intensity distribution of the light diffracted/scattered, by the particle group to be measured, of the laser beam is measured to thereby attain a desired object.

More specifically, in case a measuring angle range of the diffracted/scattered light from the particle group to be measured is fixed, the minimum value of the particle diameter to be measured can be made smaller as a wavelength of the beam to be irradiated to the particle group to be measured is shorter. When the laser beam having a wavelength in a region of 300 to 500 nm is used as the irradiation beam to be irradiated to the particle group to be measured, by measuring only the space intensity distribution of the diffracted/scattered light in the same measuring angle region as in the conventional technique, the particle size distribution in a wide range from a sub-sub-micron to several thousands $\mu$m can be accurately measured without breakpoints. Also, the laser beam having a wavelength from 300 to 500 nm is less absorbed by the blue color particles. Thus, with respect to the blue color particles, by measuring the space intensity distribution of the diffracted/scattered light in the same measuring angle region as in the conventional technique, an accurate particle size distribution can be obtained in the above-stated wide particle diameter region.

In the invention, in addition to the basic structure as explained above, the measurement optical system may be formed of a plurality of light sensors disposed in an area of a predetermined front angle in an irradiating direction of the laser beam.

Also, the measurement optical system may be formed of a converging lens for converging light diffracted/scattered by the particle group to be measured, and a ring detector disposed at a focal position of the converging lens and formed of a plurality of independent conical light receiving surfaces in the shape of a ring, half ring or ¼ ring having different radii.

Further, in case the converging lens and the ring detector are used as the forward scattered light sensors for forming the measurement optical system, only the optical axes of the converging lens and the ring detector are aligned with the optical axis of the irradiation optical system. As a result, it is possible to precisely measure the space intensity distribution of the diffracted/scattered light. Since the mutual positional relationship between the irradiation optical system and the measurement optical system need not be held constantly through the sample cell as in the case where the sideward and backward scattered light sensors are used. Thus, it is possible to measure particle size distribution in air or water in the order of sub-micron with an open system.

DETAILED DESCRIPTION OF PREFERRED EMBODIMENTS

With reference to the accompanying drawings, embodiments of the present invention are explained hereunder.

Figure 1:
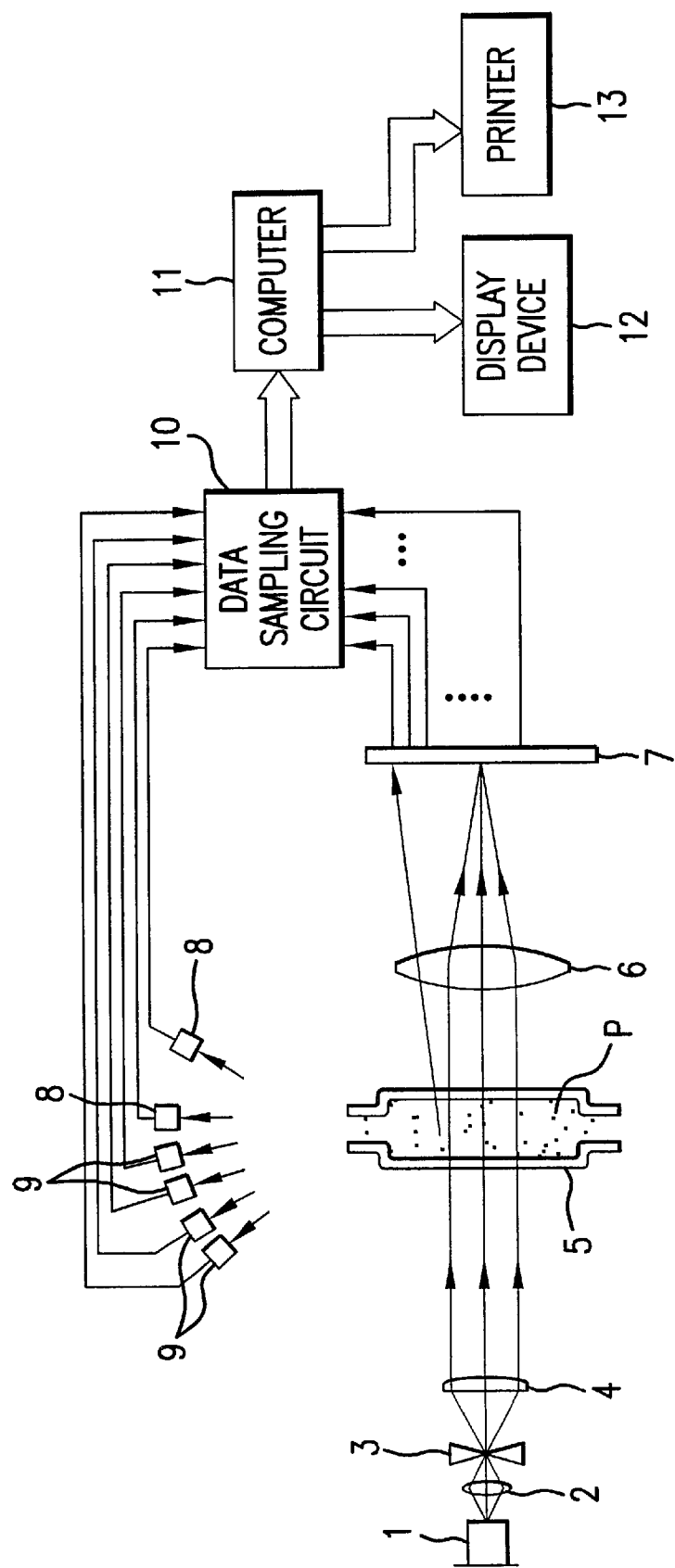
FIG. 1 is a block diagram showing a structure of an embodiment of a particle size analyzer based on the laser diffraction method according to the invention.

FIG. 1 is a block diagram showing a structure of an embodiment according to the present invention.

A semiconductor laser 1 outputs laser beam having a wavelength of about 400 nm, in the embodiment. The beam outputted from the semiconductor laser 1 is formed into parallel beam through a converging lens 2, space filter 3 and collimating lens 4, and then irradiated to a flow cell 5. A suspension formed by dispersing a particle group P to be measured in a liquid medium flows in the flow cell 5, and the laser beam is diffracted or scattered by the particle group P to be measured.

The light diffracted or scattered by the particle group P to be measured in a predetermined front angle region is detected by a ring detector 7 through a converging lens 6, and the light diffracted or scattered by the particle group P to be measured in the areas of scattering angles larger than that is detected by sideward scattered light sensors 8 and backward scattered light sensors 9. Outputs from the respective sensors are amplified and digitized by a data sampling circuit 10 formed of amplifiers and digital-to-analog converters (hereinafter referred to A/D converters) corresponding to the respective sensors, and inputted to a computer 11 as diffracted/scattered light intensity distribution data.

In the computer 11, a particle size distribution of the particle group P to be measured is calculated from the diffracted/scattered light intensity distribution data by the above-mentioned known method. The results can be displayed in a display device 12 or printed by a printer 13.

According to the embodiment of the invention, the irradiation beam with respect to the particle group P to be measured is a laser beam of a single wavelength having about 400 nm. Moreover, since a space intensity distribution of the diffracted/scattered light of the irradiation laser beam by the particle group P is measured by a measurement optical system of one system, an accurate particle size distribution with no break-points can be obtained in a wide range from a fine-particle having a diameter of the order of sub-sub-micron to a large particle having a diameter of the order from several hundreds of Am to several thousands of $\mu$m.

Figure 2A:
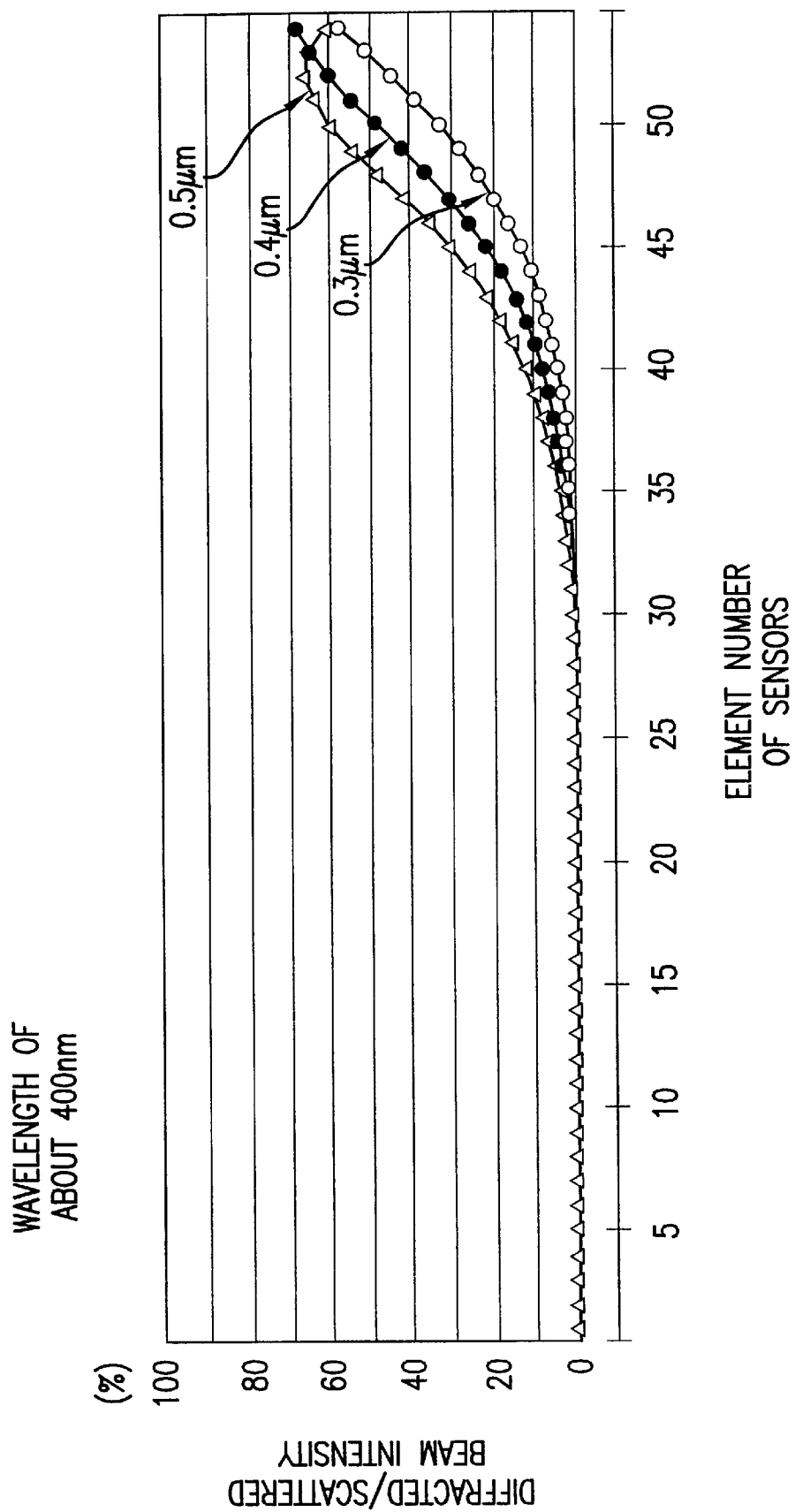
FIGS. 2(A) and 2(B) are graphs explaining experimental results for confirming difference of measured results in a space intensity distribution of light diffracted/scattered by fine particles when irradiation beam having different wavelengths is irradiated, wherein FIG. 2(A) employs a laser beam of a wavelength of about 400 nm, and FIG. 2(B) employs a laser beam of a wavelength of about 700 nm.
Figure 2B:
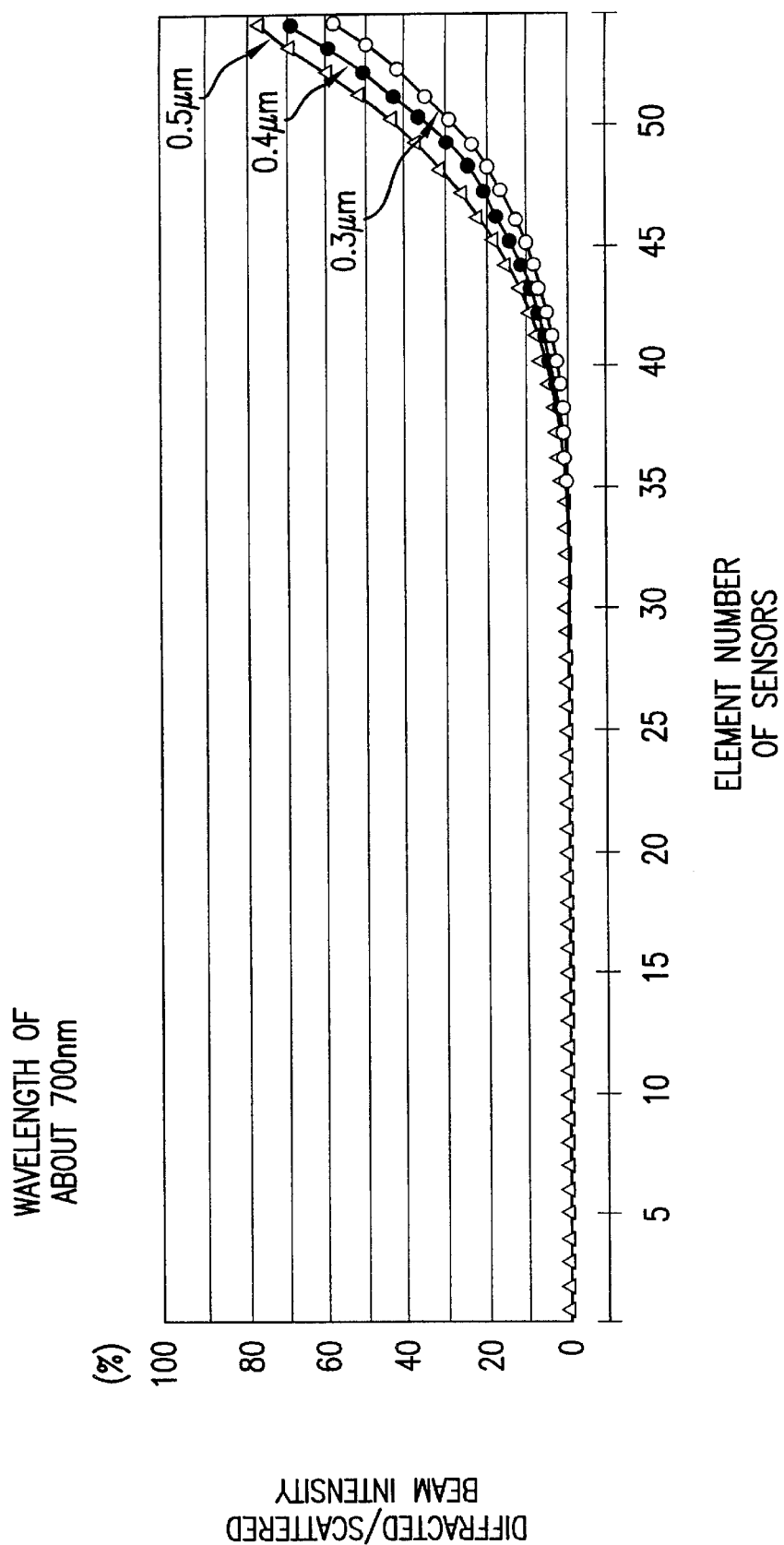

FIGS. 2(A) and 2(B) are graphs showing experimental results for confirming differences of the measured results of the space intensity distributions of the diffracted/scattered light according to the differences of wavelengths of the laser beam irradiated to the particle group P to be measured (in a front angle range up to about 40°). In the experiments, the space intensity distributions of the diffracted/scattered light by the particles having various particle diameters were measured with the same measurement optical system, by using powders having particle diameters of 0.3 $\mu$m, 0.4 $\mu$m and 0.5 $\mu$m, respectively, as particle groups to be measured, and through the irradiations of the laser beam of about 400 nm and about 700 nm, respectively. FIG. 2(A) is a graph showing the results measured when a laser beam having a wavelength of about 400 nm was irradiated; and FIG. 2(B) is a graph showing the results measured when a red color laser beam having a wavelength of about 700 nm was irradiated.

As apparent from the graphs, in the red color laser beam, it is difficult to identify the respective particles having diameters smaller than 0.5 $\mu$m, while in the laser beam having the wavelength of about 400 nm, there are observed significant differences in the space intensity distributions of the light diffracted/scattered by the particles of the respective diameters of 0.3 to 0.5 $\mu$m. Such a phenomenon can be also observed with respect to the sideward scattered light and the backward scattered light over 40°. Thus, by measuring the space intensity distributions of the diffracted/scattered light of the laser beam having wavelengths from 300 to 500 nm for the particle group to be measured in a wide angle range including the front side, lateral side and back side, it is possible to identify difference in the particle diameters of the order of a sub-sub-micron and obtain a particle size distribution from a particle of an extremely fine diameter to a particle of a large diameter without any discontinuous point and with a good repeatability.

Figure 3A:
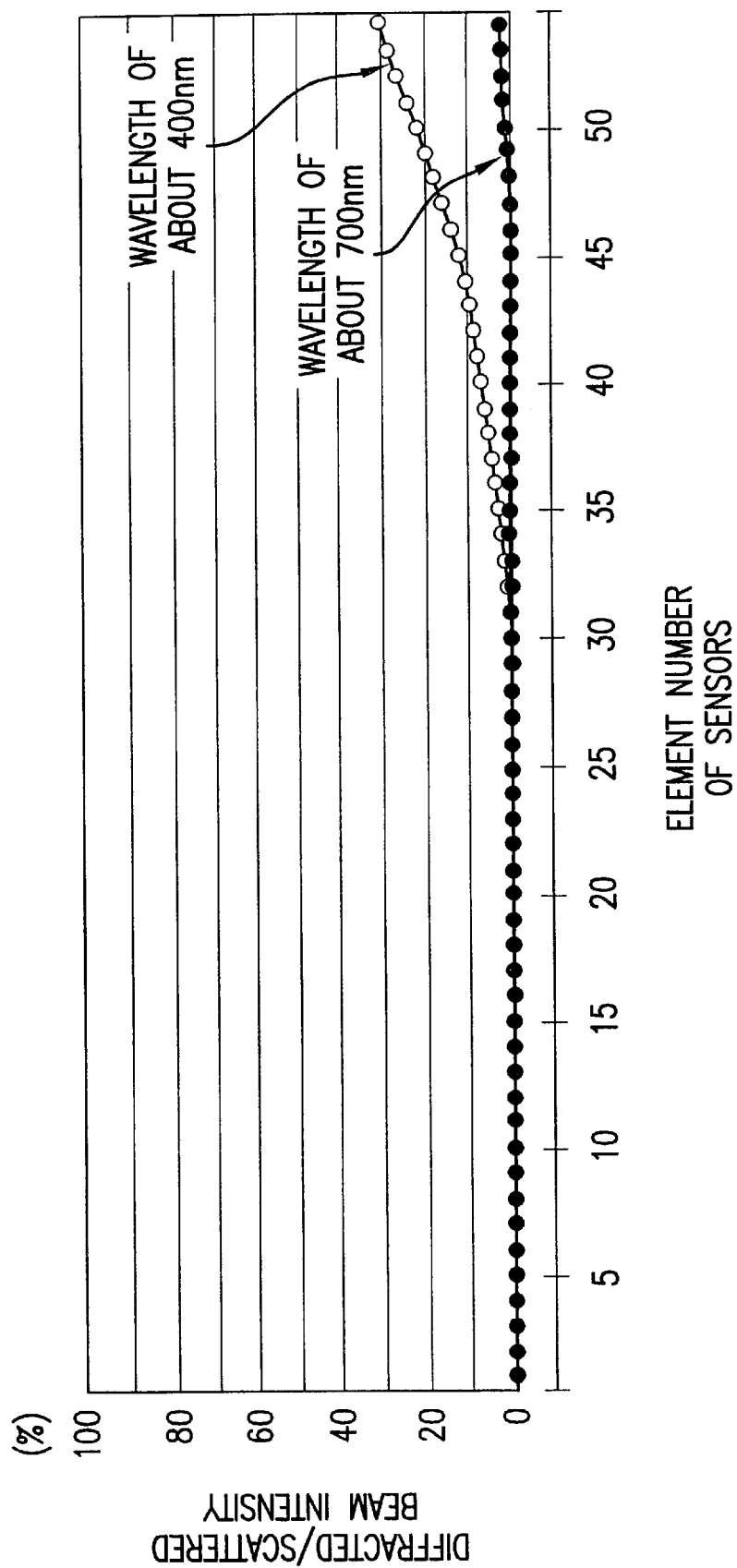
FIG. 3(A) is a graph showing measured results of a space intensity distribution of the diffracted/scattered light by blue color particles, wherein irradiation beam having wavelengths of about 400 and 700 nm is used.
Figure 3B:
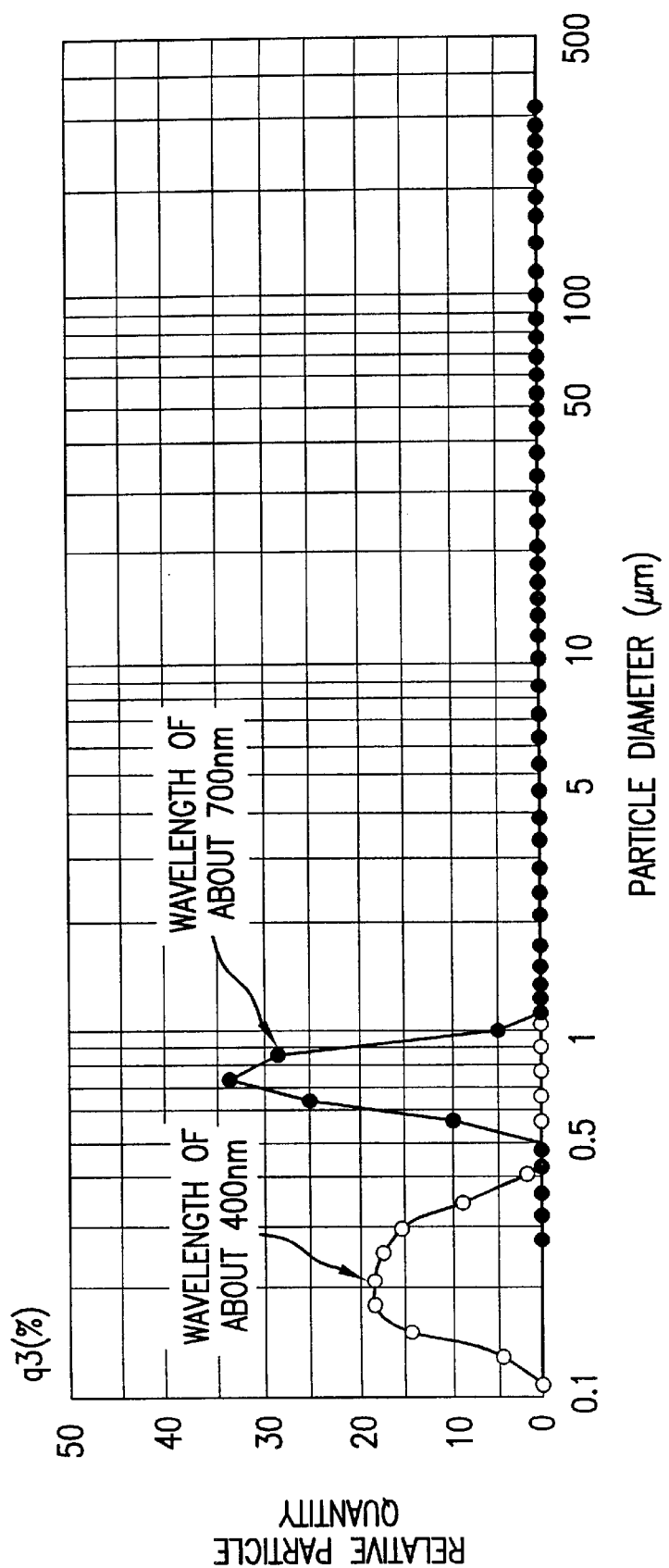
FIG. 3(B) is a graph showing a particle size distribution calculated based on the measured results in FIG. 3(A)

Also, FIGS. 3(A) and 3(B) are explanatory graphs of measured results of the particle size distribution of an indigo paint by using laser beam having a wavelength of about 400 nm and a wavelength of about 700 nm, respectively, with the other conditions being the same. FIG. 3(A) is a graph showing measured results of the space intensity distribution of diffracted/scattered light; and FIG. 3(B) is a graph showing calculated results of a particle size distribution, i.e. frequency distribution, by using the measured results of the space intensity distribution.

As shown in FIGS. 3(A) and 3(B), the red color laser beam having a wavelength of about 700 nm can be easily absorbed by blue color particles, so that it is difficult to accurately measure the space intensity distribution of the diffracted/scattered light. On the contrary, since absorption of laser beam having a wavelength of about 400 nm is less than that in the blue particles, it is possible to accurately measure the space intensity distribution of the diffracted/scattered light. Thus, the particle size distribution is also accurate. Therefore, there can be observed a big difference when compared with a case where the laser beam having the wavelength of about 700 nm is used.

Incidentally, in the above-described embodiment of the invention, the diffracted/scattered light from the particle group P was measured through the forward scattered light sensor formed of the converging lens 6 and the ring detector 7, the sideward scattered light sensors 8 and the backward scattered light sensors 9. However, as occasion demands, the diffracted/scattered light may be measured only in the predetermined front angle range. Thus, in the present invention, there can be employed a structure having only the forward scattered light sensor, and a structure having the forward scattered light sensor and the sideward scattered light sensor.

Figure 4:
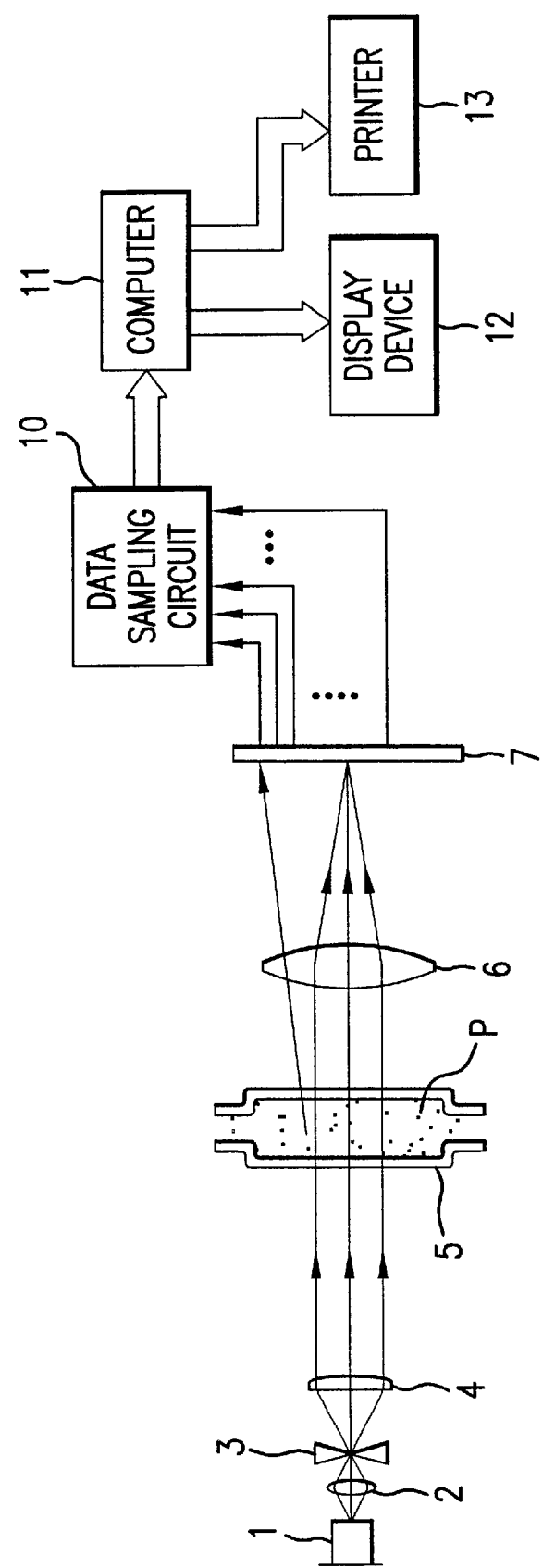
FIG. 4 is an explanatory diagram showing a basic structure of a measuring portion of the particle size analyzer based on the laser diffraction method.

FIG. 4 is a block diagram showing a structure of another embodiment according to the invention. The same portions and members as those in FIG. 1 are represented by the same reference numerals, and their explanations are omitted.

The outputted beams having a wavelength of about 400 nm from a semiconductor laser 1 are formed into parallel beams through a converging lens 2, space filter 3 and collimating lens 4, and then irradiated to a flow cell 5. The laser beams are diffracted or scattered by the particle group P to be measured.

Only the light diffracted/scattered by the particle group P to be measured within a predetermined front angle region, i.e. only light within the region of an angle in the order of, for example, about 40° in the front thereof, is converged by a converting lens 6; diffracted/scattered ring-shape images are formed at a focal position thereof; and the space intensity distribution of the diffracted/scattered light is detected by a ring detector 7 disposed at the focal position of the converging lens 6. The ring detector 7 is a light detector having the same structure as that used in the conventional measuring apparatus of this type, wherein a plurality of independent light receiving surfaces, such as a ring, semi-ring or ¼ ring, having different radii is concentrically disposed. Outputs relating to incident light quantities to the respective light receiving surfaces of the ring detector 7 are amplified and digitized by a data sampling circuit 10 including amplifiers and A/D converters corresponding to the respective outputs, and then inputted to a computer 11 as the diffracted/scattered light intensity distribution data.

In the computer 11, the particle size distribution of the particle group P to be measured is calculated from the diffracted/scattered light intensity distribution data by the above-mentioned known method. The calculated results can be displayed on a display device 12 or printed out by the printer 13.

According to the embodiment of the invention, since the beam to be irradiated to the particle group P to be measured is laser beam having a wavelength of about 400 nm, by measuring only the space intensity distribution of the diffracted/scattered light within a front region of about 40°, a particle diameter in the order of sub-micron can be measured from the space intensity distribution thereof.

As experiments for confirming difference of measured results in the space intensity distribution of the diffracted/scattered light caused by different wavelengths of the laser beam to be irradiated to the particle groups P to be measured, the space intensity distribution of the light diffracted or scattered by sample particle groups P including only 0.3 $\mu$m, 0.4 $\mu$m and 0.5 $\mu$m was measured by the ring detector 7 under the same conditions except that a semiconductor laser 1 having an output wavelength of about 400 nm was used as a light source of an irradiation optical system in one case, and a semiconductor laser 1 having an output wavelength of about 700 nm was used as a light source in another case.

As a result, the same graphs as those shown in FIGS. 2(A) and 2(B) were obtained. Thus, it is confirmed that the particles having a diameter of the order of sub-micron can be sufficiently measured by using, as the light source of the irradiation optical system, the semiconductor laser 1 having the output wavelength of about 400 nm and by measuring the space intensity distribution of the light diffracted or scattered by the particle group P only within the front region of about 40°, through the converging lens 6 and ring detector 7.

In the embodiments as described hereinabove, the space intensity distribution of the diffracted/scattered light was measured while the particle group P to be measured flows through the flow cell 5. However, in the present invention, since the particles having a diameter of the order of sub-micron can be measured without using the sideward and backward scattered light sensors, it is also possible to measure particles having a diameter of the order of sub-micron by directly irradiating the laser beam to particles floating in air and in water, a so-called open system measuring method, without providing the above-stated flow cell 5 or a sample cell for containing therein the particle group P to be measured.

Figure 5:
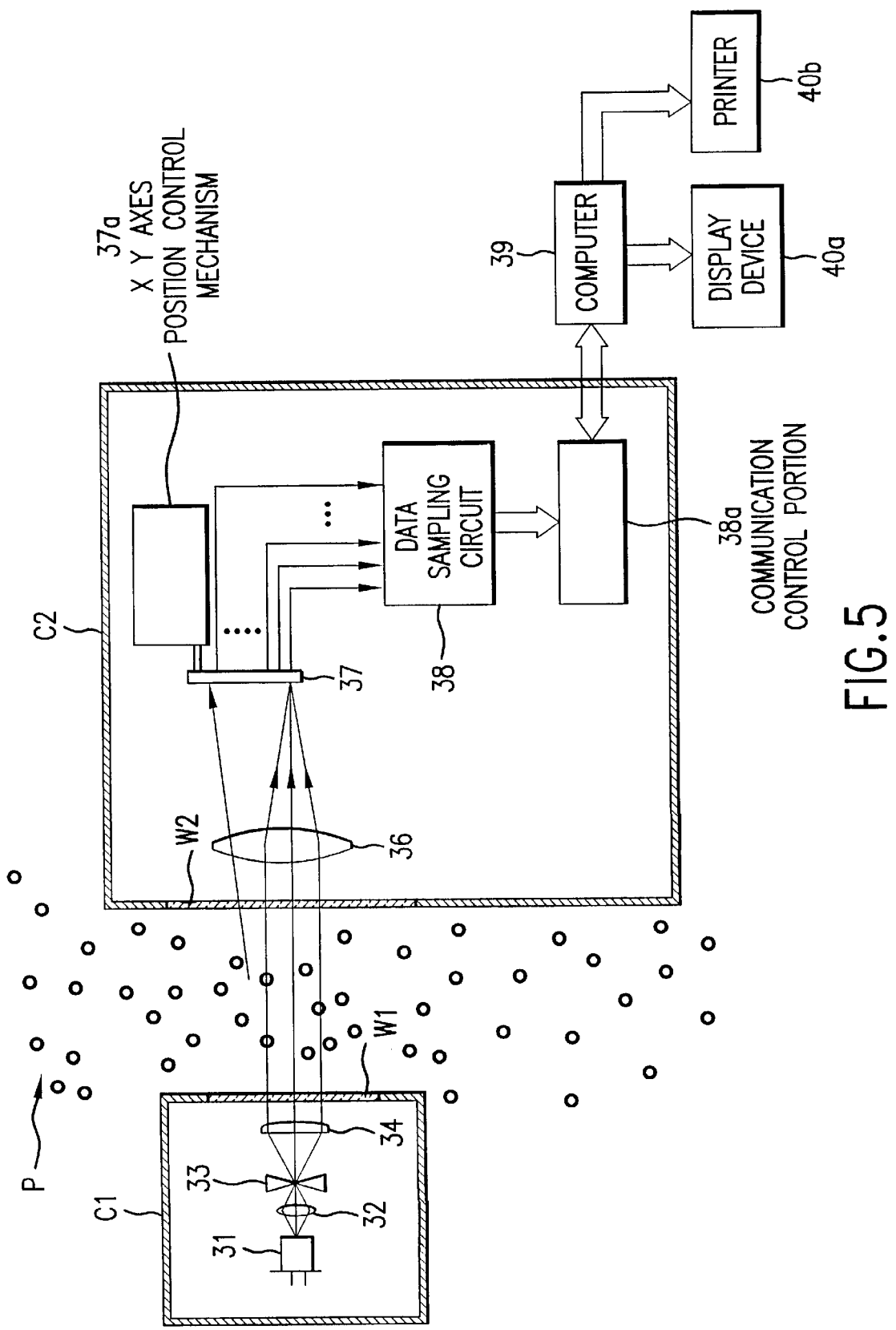
FIG. 5 is a block diagram showing a structure of another embodiment of the invention, wherein a measurement system of an open system is employed.
Figure 6:
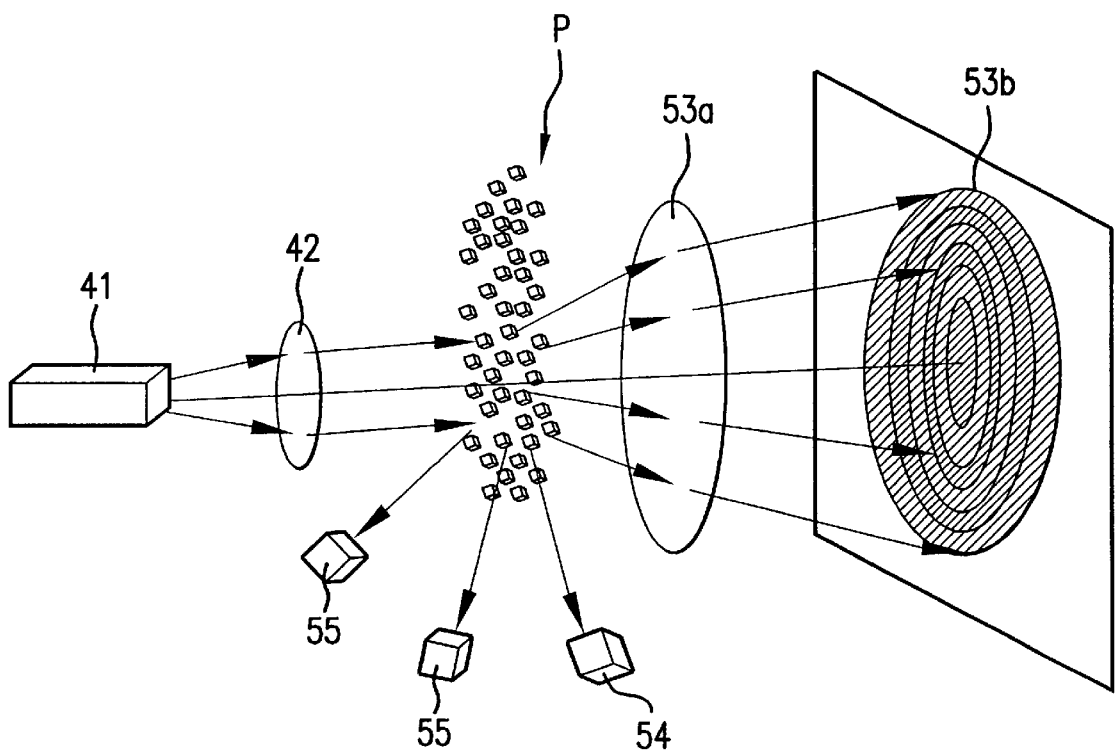
FIG. 6 is a block diagram showing a structure of a conventional particle size analyzer based on the laser diffraction method, wherein laser beam of wavelengths of 600 to 800 nm is used.
Figure 7:
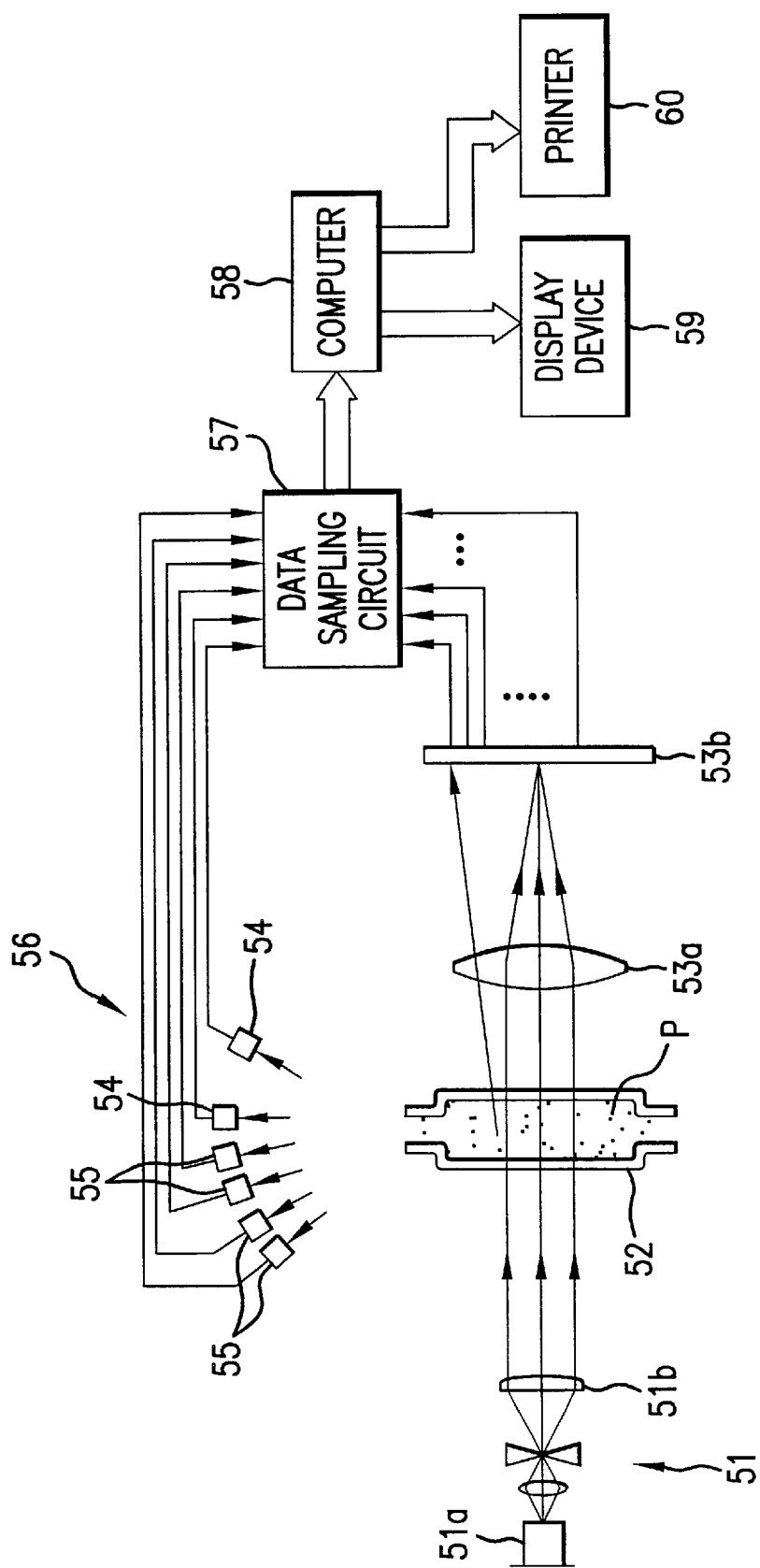
FIG. 7 is a block diagram showing a structure of another conventional measuring apparatus, wherein particles having diameters of the order of sub-micron can be measured.
Figure 8:
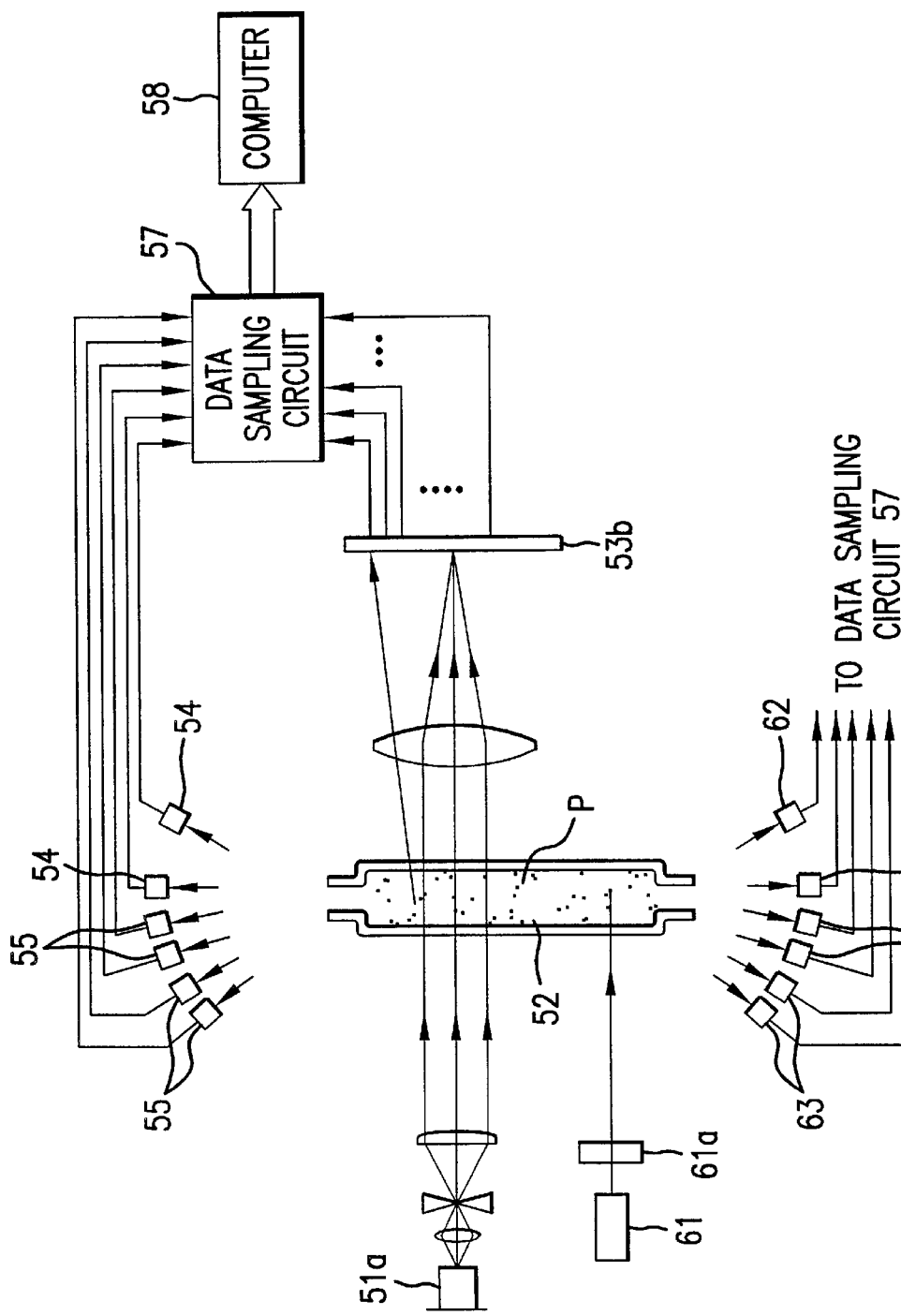
FIG. 8 is a block diagram showing a structure of still another conventional measuring apparatus, wherein particles having diameters of the order of sub-sub-micron can be measured.

FIG. 5 is a block diagram showing a structure of a further embodiment of the invention, wherein a measuring system is an open system. In the embodiment, an irradiation optical system and a measurement optical system are separated and housed in a case C1 and a case C2, respectively.

More specifically, the irradiation optical system including a semiconductor laser 31 having an output wavelength of about 400 nm, a converging lens 32, a space filter 33 and a collimating lens 34 as in the above-stated embodiments is housed in the case C1, and parallel laser beam is irradiated toward the outside through a window W1 made of a translucent material and provided to the case C1.

On the other hand, the measurement optical system including a converging lens 36 and a ring detector 37 disposed at a focal position thereof is housed in the other case C2 to which a window W2 made of the translucent material is provided on a side of the converging lens 36. Also, in the case C2, there are housed an xy axis position control mechanism 37a for controlling a position of the ring detector 37 vertically and horizontally, a data sampling circuit 38 including amplifiers and A/D converters, and a communication/control portion 38a for communicating with a computer 39 disposed outside and controlling respective circuits in the case C2 based on a command from the computer 39. The measured results of the space intensity distribution of the diffracted/scattered light measured by the ring detector 37 are inputted to the computer 39 through the data sampling circuit 38 and communication/control portion 38a to calculate the particle size distribution. The results of the particle size distribution calculated by the computer 39 are supplied to the display device 40a or the printer 40b to display or print out.

When the particle size distribution is measured according to the embodiment, as shown in FIG. 5, the case C1 and the case C2 are disposed with an appropriate space therebetween so that the window W1 and the window W2 face each other in air or in water where a particle group P to be measured is floating, and then optical axes of the irradiation optical system and the measurement optical system are allowed to coincide with each other. Thus, laser beam having a wavelength of about 400 nm is irradiated to the particle group P to be measured through the window W1, and the diffracted/scattered light generated therefrom are converged on the light receiving surface of the ring detector 37 by the converging lens 36 through the window W2 to measure the space intensity distribution thereof. The computer 39 receives the space intensity distribution data through the communication/control portion 38a to calculate the particle size distribution of the particle group P to be measured.

Especially, a noteworthy point in the above embodiment is to dispose only the case C1 having the irradiation optical system and the case C2 having the measurement optical system in air or in water where the particle group P to be measured is floating without providing a cell for flowing or containing the particle group P to be measured therein. Instead, the particle size distribution of the particle group P to be measured can be measured to a fine particle region of the order of sub-micron. A characteristic of the embodiment resides in that the particle size can be measured to a region of the order of sub-micron by employing only the converging lens 36 and the ring detector 37 as the forward scattered light sensor without providing the sideward and backward scattered light sensors. Taking advantage of this point, for example, it is possible to easily measure harmful floating particles discharged from a diesel engine or the like.

According to the invention, the semiconductor laser for outputting a laser beam of a single wavelength having a wavelength of 300 to 500 nm is used as a light source; the diffracted/scattered light obtained by irradiating the laser beam to the particle group P to be measured are detected at the front, side and back to measure the space intensity distribution; and the particle size distribution of the particle group P to be measured is calculated from the above-measured results, so that the particle size distribution with no break-points can be obtained in a wide range from a fine particle having a diameter of the order of sub-sub-micron to a large particle having a diameter of the order from several hundreds to several thousands of μm with a good reliability.

It is also possible to accurately measure the particle size distribution in the above-mentioned wide range for the blue color particles in which particle size distribution has been difficult to be accurately measured by the conventional red color laser beam.

Also, the measuring apparatus according to the invention is simpler in its structure and cheaper in its cost when compared with conventional apparatuses wherein two types of light sources and two measurement optical systems corresponding thereto are used, or a measurement system based on the other measuring method is added.

Also, according to the present invention, even if the semiconductor laser beam having a wavelength in a range of 300 to 500 nm is used as a light source of the irradiation optical system and the diffracted/scattered light of the outputted laser beam by the particle group is measured by only light sensors disposed in a predetermined front angle region, it is possible to measure the particle diameter of the order of sub-micron. Thus, even if the apparatus of the invention has a measuring region equal to that in the conventional apparatus, the structure of the measurement optical system is simplified to thereby provide a particle size analyzer of a cheaper cost when compared with the conventional apparatus.

Further, in case the converging lens and the ring detector are used as the forward scattered light sensors, only the optical axis of the irradiation optical system is allowed to coincide with the measurement optical system, so that a particle diameter of the order of sub-micron can be measured without holding mutual positional relationships between the irradiation optical system and the particle group to be measured and between the particle group to be measured and the measurement optical system as in the case where the sideward and backward scattered light sensors are used. Since it is possible to measure the particle sizes of the order of sub-micron with the open system without using the sample cell where the sample flows or is contained, there can be provided a particle size analyzer for sufficiently coping with measurement of harmful floating particles discharged from a diesel engine or the like.

While the invention has been explained with reference to the specific embodiments of the invention, the explanation is illustrative and the invention is limited only by the appended claims.

What is claimed is:

1. A particle size analyzer based on laser diffraction method, comprising:

an irradiation optical system for irradiating laser beam to particles, said irradiation optical system having a semiconductor laser in an output beam wavelength of 300 to 500 nm as a light source and a casing with a window containing the semiconductor laser;

a measurement optical system situated near the irradiation optical system for measuring a space intensity distribution by receiving light diffracted/scattered by particles of the laser beam from the irradiation optical system, said measurement optical system including a plurality of light sensors disposed in an area of a predetermined front angle in an irradiating direction of the laser beam, a converging lens for converging light diffracted/scattered by a particle group to be measured, a ring detector disposed at a focal position of the converging lens and formed of a plurality of independent conical light receiving surfaces in a shape of a ring, half ring or ¼ ring having different radii, an xy axes position control mechanism connected to the ring detector, and a casing with a window, said casings being spaced apart from each other so that the windows face to allow the laser beam to pass through the windows; and an operation portion connected to the measurement optical system for obtaining a particle size distribution of the particles from results measured by the measurement optical system.

2. A particle size analyzer based on laser diffraction method according to claim 1, wherein said semiconductor laser has an output beam wavelength of 300 to 400 nm.

* * * * *